(12) United States Patent
Schneider et al.

(10) Patent No.: US 7,317,951 B2
(45) Date of Patent: Jan. 8, 2008

(54) ANCHOR FOR MEDICAL IMPLANT PLACEMENT AND METHOD OF MANUFACTURE

(75) Inventors: Richard Lee Schneider, Livonia, MI (US); Nader Najafi, Ann Arbor, MI (US); David J. Goetzinger, Livonia, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 395 days.

(21) Appl. No.: 10/898,053

(22) Filed: Jul. 24, 2004

(65) Prior Publication Data

US 2005/0065589 A1 Mar. 24, 2005

Related U.S. Application Data

(60) Provisional application No. 60/491,002, filed on Jul. 30, 2003, provisional application No. 60/489,974, filed on Jul. 25, 2003.

(51) Int. Cl.
*A61N 1/05* (2006.01)
(52) U.S. Cl. .................................. 607/126; 606/213
(58) Field of Classification Search ............... 600/375; 607/126–128
See application file for complete search history.

(56) References Cited

U.S. PATENT DOCUMENTS

| 5,300,107 | A | * | 4/1994 | Stokes et al. | 607/126 |
| 5,853,422 | A | * | 12/1998 | Huebsch et al. | 606/213 |
| 6,309,350 | B1 | * | 10/2001 | VanTassel et al. | 600/300 |
| 6,328,699 | B1 | * | 12/2001 | Eigler et al. | 600/486 |
| 2002/0077555 | A1 | * | 6/2002 | Schwartz | 600/486 |
| 2004/0116992 | A1 | * | 6/2004 | Wardle et al. | 607/116 |

* cited by examiner

*Primary Examiner*—Kristen D. Mullen
(74) *Attorney, Agent, or Firm*—Hartman & Hartman, P.C.; Gary M. Hartman; Domenica N. S. Hartman (57) ABSTRACT

An anchor and procedure for placing a medical implant, such as for monitoring physiological parameters. The anchor includes a central body in which a medical implant can be received. Arms and members extend radially from first and second ends, respectively, of the central body. Each member defines a leg extending toward distal portions of the arms to provide a clamping action. The anchor and its implant are placed by coupling first and second guidewires to first and second portions of the anchor, placing an end of a delivery catheter in a wall where implantation is desired, inserting the anchor in the catheter with the guidewires to locate the anchor within the wall, deploying the arms of the anchor at one side of the wall followed by deployment of the members at the opposite side of the wall, and thereafter decoupling the guidewires from the anchor.

52 Claims, 6 Drawing Sheets

ANCHOR FOR MEDICAL IMPLANT PLACEMENT AND METHOD OF MANUFACTURE

CROSS REFERENCE TO RELATED APPLICATIONS

This application claims the benefit of U.S. Provisional Application Nos. 60/489,974, filed Jul. 25, 2003, and 60/491,002, filed Jul. 30, 2003.

STATEMENT REGARDING FEDERALLY SPONSORED RESEARCH

This invention was made with Government support under Contract No. NNC04CA10C awarded by National Astronautics and Space Agency. The Government has certain rights in the invention.

BACKGROUND OF THE INVENTION (1) Field of the Invention

The present invention relates generally to implantable medical devices, such as of the types for monitoring physiological parameters. More particularly, the invention relates to an anchor for a medical implant, a method of manufacturing anchors, and a method of placing a medical implant, wherein the anchor and method are suitable for use in procedures performed to diagnose, monitor, and/or treat cardiovascular diseases, including procedures performed to monitor pressure in the left side of the heart.

(2) Description of the Related Art

Congestive Heart Failure (CHF), a condition in which the heart fails to pump efficiently, currently affects about 4.7 million patients (over 400,000 new patients per year in the U.S.), accounts for about 5 to 10% of all hospitalizations, and costs over $38 billion in the U.S. Following diagnosis of congestive heart failure, physicians typically monitor disease progression on a continuing basis to better tailor treatment. The best course of action for a tailored treatment involves monitoring of the pressures of the left side of the heart, particularly left ventricular end diastolic pressure (LVEDP, also known as left ventricular filling pressure) and mean left atrium pressure (MLA). These pressures are recognized as the best parameters for characterizing congestive heart failure in patients. Clinical evaluation of LVEDP or MLA is currently limited to a cardiac catheterization procedure, which provides a snapshot of pressure data a few times per year at most, carries morbidity, and is expensive.

Monitoring the pressures of the left side of the heart is a very challenging task for many reasons, most importantly the potentially fatal outcome of any thrombi caused by the implant. Implants can be made using many technologies, though preferred methods typically include MEMS (Microelectromechanical systems) devices and technologies. Such miniaturized implants can provide chronic, continuous biopressure measurements and support the trend toward home health monitoring. Pressure monitoring systems have two primary components: the implant comprising an implantable telemetric pressure sensor that is batteryless or makes use of a small battery, and a companion hand-held reader. The implant further includes custom electronics for processing the output of the sensor and an antenna for telemetry and, if necessary or desired, for tele-powering the sensor. Telemetry and tele-powering can be achieved via various techniques, including but not limited to magnetic telemetry (including RF), acoustic waves, ultrasonic waves, with the currently preferred technique typically being magnetic telemetry. The reader transmits power to the sensor, and the sensed pressure is in turn transmitted back to the reader. Data collected from the sensor can then be used by a physician to tailor the treatment of the patient. In some cases, the implant may also be configured or adapted to perform additional functions, such as delivering a drug or an electric signal to the muscles/nerves.

Though the above evidences that significant advances have been achieved for implants capable of diagnosing, monitoring, and/or treating cardiovascular diseases, further improvements are desired, particularly pertaining to the delivery and anchoring of such medical implants within the heart for monitoring heart pressures.

BRIEF SUMMARY OF THE INVENTION

The present invention provides an anchor for a medical implant, a method of manufacturing the anchor, and a procedure for placing a medical implant such as for monitoring physiological parameters. The invention is particularly directed to implantation of physiologic sensors/actuators for diagnosing and/or monitoring and/or treating cardiovascular diseases, such as congestive heart failure and congenital heart disease.

The anchor of this invention includes a central body in which a medical implant can be received. The central body has an axis and first and second ends in oppositely-disposed first and second directions, respectively, along the axis of the central body. A plurality of arcuate arms extend substantially radially from the first end of the central body, and each arcuate arm has a distal portion extending in the second direction relative to the central body. A plurality of arcuate members extend substantially radially from the second end of the central body, and each arcuate member defines a leg extending in the first direction toward the distal portions of the arcuate arms. The anchor can be fabricated so that two or more of the its components are integral portions as a result of being machined, preferably laser cut, from a monolithic body.

The anchor makes possible a method for placing a medical implant. Such a method involves coupling at least a first guidewire to a first portion of an anchor in which the medical implant is received and coupling at least a second guidewire to a second portion of the anchor. An end of a delivery catheter is then placed within an opening in an internal wall of a human body, and the anchor is inserted in the delivery catheter with the first and second guidewires so as to place the anchor within the internal opening of the body. The anchor is inserted so that a plurality of arcuate arms extending substantially radially from the first portion of the anchor are released from the end of the delivery catheter. The first and second guidewires are then retracted through the delivery catheter so that the arcuate arms of the anchor contact a first side of the internal wall. Thereafter, the delivery catheter can be retracted to release a plurality of arcuate members extending substantially radially from the anchor. Each arcuate member defines a leg contacting an oppositely-disposed second side of the internal wall so as to secure the anchor and the medical implant received therein to the internal wall. Finally, the second guidewire is decoupled from the second portion of the anchor, and the first guidewire is decoupled from the first portion of the anchor.

In view of the above, it can be seen that the present invention provides an uncomplicated anchor and procedure of placing an implantable medical devices for monitoring physiological parameters. The configuration of the anchor addresses delivery issues, including delivery method, delivery equipment, implant design, and anchor location, that arise when employing implantable physiologic sensors/actuators to diagnose and/or monitor and/or treat cardiovascular diseases such as congestive heart failure and congenital heart disease. Notably, the anchor and its delivery find application in very challenging application of monitoring the pressure of the left side of the heart. Medical implants that can be placed and anchored in accordance with this invention can operate wirelessly or can be connected to other devices (such as pacemakers) using electrical wires (e.g., pacemaker leads, polymer based flex cables, or wires) or other types of communications means (e.g., ultrasonic, optical, or electrophysiology signals).

Other objects and advantages of this invention will be better appreciated from the following detailed description.

DETAILED DESCRIPTION OF THE INVENTION

FIGS. 1 through 5 depict an anchor 10 suitable for delivering and securing a medical implant 12 to a wall 14, such as a wall of a cardiovascular organ, in accordance with an embodiment of the present invention. In a notable example, the wall 14 is an atrial septum and the implant 12 measures physiological parameters of the heart, such as LVEDP or MLA pressure. The implant 12 may be any one of a variety of types of implants currently known or developed in the future, and the scope of the present invention is not limited in any way by the type and operation of the implant 12.

The anchor 10 is represented in the Figures as having an annular-shaped central body 16 that defines a bore 17 in which the implant 12 is received. The central body 16 has oppositely-disposed first and second ends 18 and 20 corresponding to oppositely-disposed first and second directions along the axis of the central body 16. Arcuate arms 22 extend substantially radially and in the first direction from the first end 18 of the central body 16, and arcuate members 24 extend substantially radially and in the second direction from the second end 20 of the central body 16. As can be seen from FIG. 3, each arm 22 and arcuate member 24 lies in a plane containing the axis of the central body 16. As also evident from FIG. 3, each arm 22 is axially aligned with one of the arcuate members 24 so as to lie in the same plane as the arcuate member 24.

Figure 1:
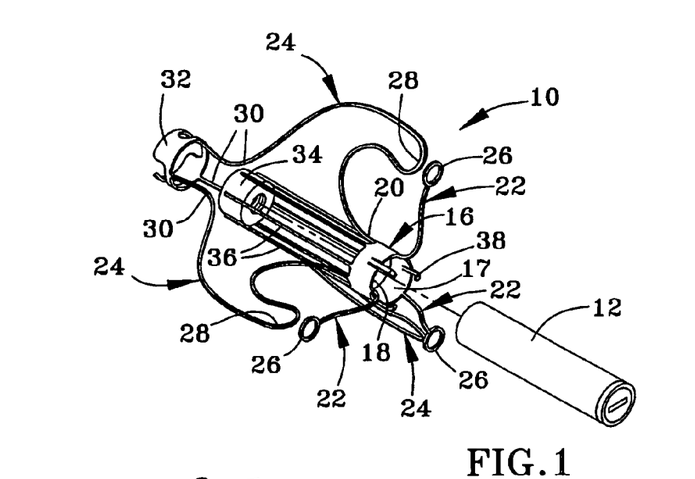
FIGS. 1 through 3 are perspective, side, and end views, respectively, of an anchor for a medical implant in accordance with an embodiment of this invention.
Figure 2:
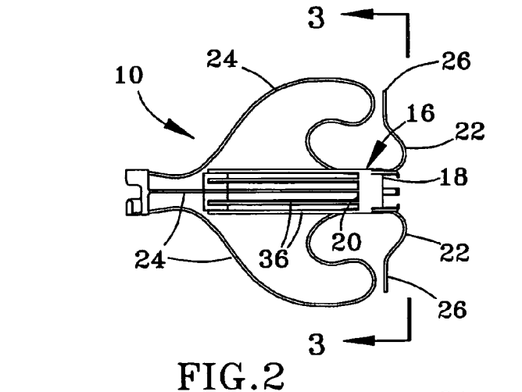
Figure 3:
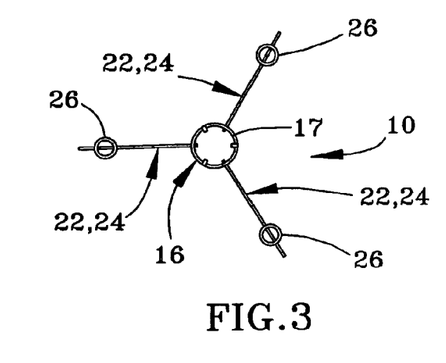
Figure 4:
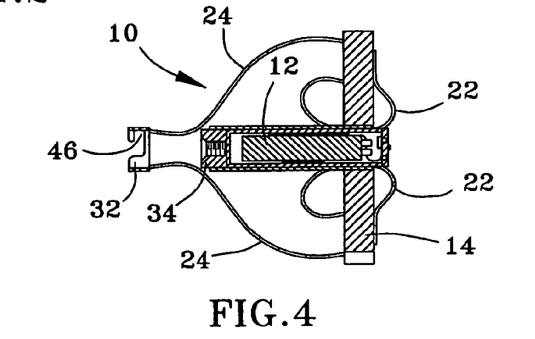
FIG. 4 is a cross-sectional view showing a medical implant anchored to a wall with the anchor of FIGS. 1 through 3.

Each arm 22 has a distal portion extending in the second direction relative to the central body 16, terminating in a pad 26 oriented substantially transverse to the axis of the central body 16. Each arcuate member 24 defines a leg 28 that extends in the first direction toward the pads 26 of the arms 22, and has a distal portion 30 that extends in the second direction from its respective leg 28. As a result of the arms 22 and arcuate members 24 being axially aligned with each other, the pads 26 of the arms 22 oppose the legs 28 of the arcuate members 24, such that the pads 26 and legs 28 cooperate to clamp the wall 14 as seen in FIG. 3, such that the anchor 10 is able to resist axial and rotating forces that might dislodge the anchor 10 and its implant 12. The pads 26 are depicted as having ring-shapes to help distribute the clamping force across a larger area of the wall 14 and promote the overall stability of the anchor 10, though other shapes and configurations are foreseeable for the pads 26. As will be evident from the following description of the implantation procedure, the circular shape of the pads 26 also helps prevent dead-ending during delivery in the anchor 10 and its implant 12. In addition to the arms 22 and arcuate members 24, the anchor 10 may include a mesh (not shown) to promote tissue growth and anchoring.

The arcuate members 24 support a first ring 32 at their distal portions 30, such that the ring 32 is axially spaced from the second end 20 of the central body 16. A second ring 34 is axially spaced from the second end 20 of the central body 16 so as to be located between the central body 16 and the first ring 32. A number of struts 36 extend from the second end 20 of the central body 16 to secure the second ring 34 to the central body 16. As evident from FIG. 4, the implant 12 is placed within the central body 16 and a cage defined by the struts 36. One end of the implant 12 abuts the second ring 34, while the opposite end of the implant 12 is secured to the central body 16 with fingers 38 that are crimped over the opening of the bore 17 in which the implant 12 is received to retain the implant 12 within the anchor 10. The fingers 38 can be initially formed to be open or temporarily moved away to allow the implant 12 to be placed inside the bore 17 of the central body 16. This low-profile configuration minimizes the diameter required of a catheter (44 in FIG. 5) used to delivery the anchor 10 and implant 12, and advantageously results in the anchor 10 exerting minimal stress on the implant 12.

Figure 5:
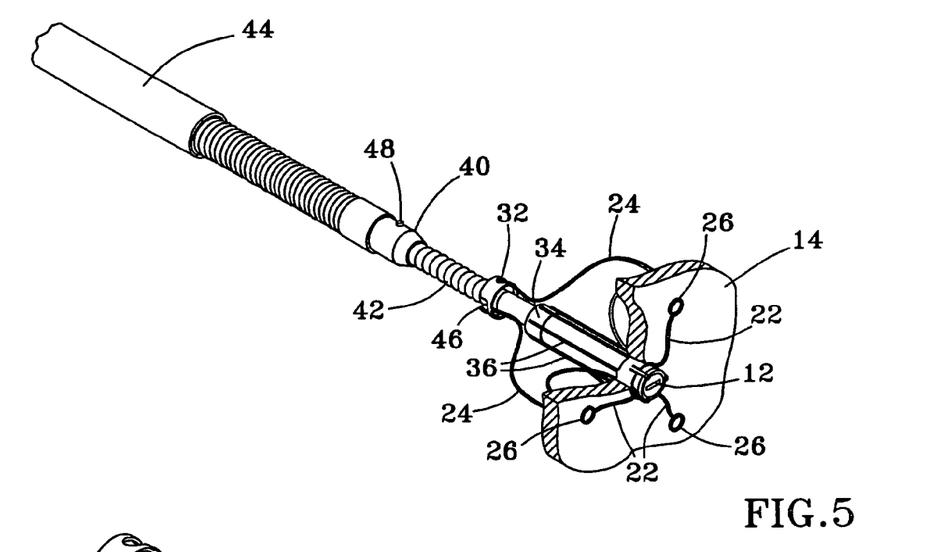
FIG. 5 is a perspective view showing the use of a delivery catheter and two guidewires in the process of placing the anchor and medical implant in a wall in accordance with FIG. 4.
Figure 7:
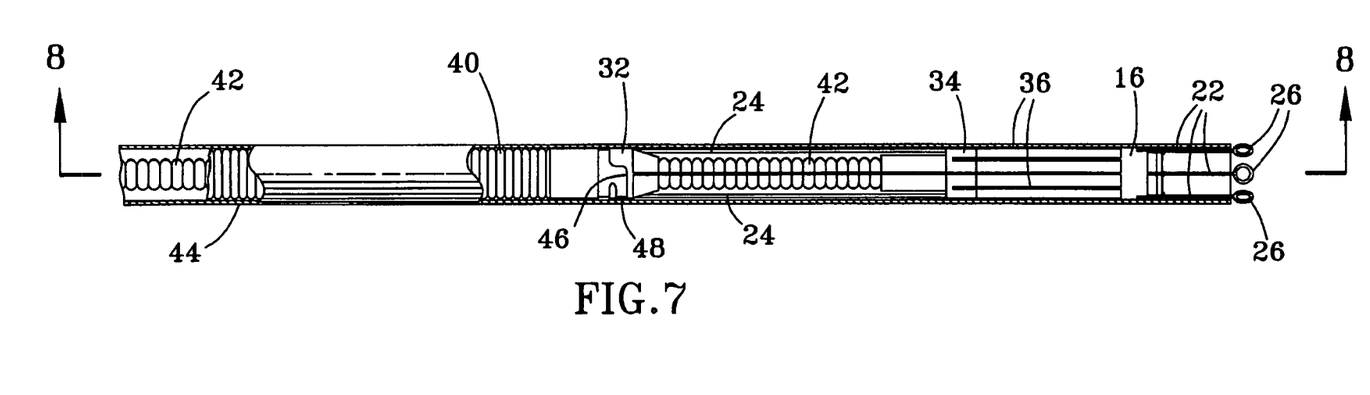
FIGS. 7 and 8 are side and cross-sectional views, respectively, showing an assembly comprising the delivery catheter, guidewires, anchor and medical implant of FIG. 4.
Figure 8:
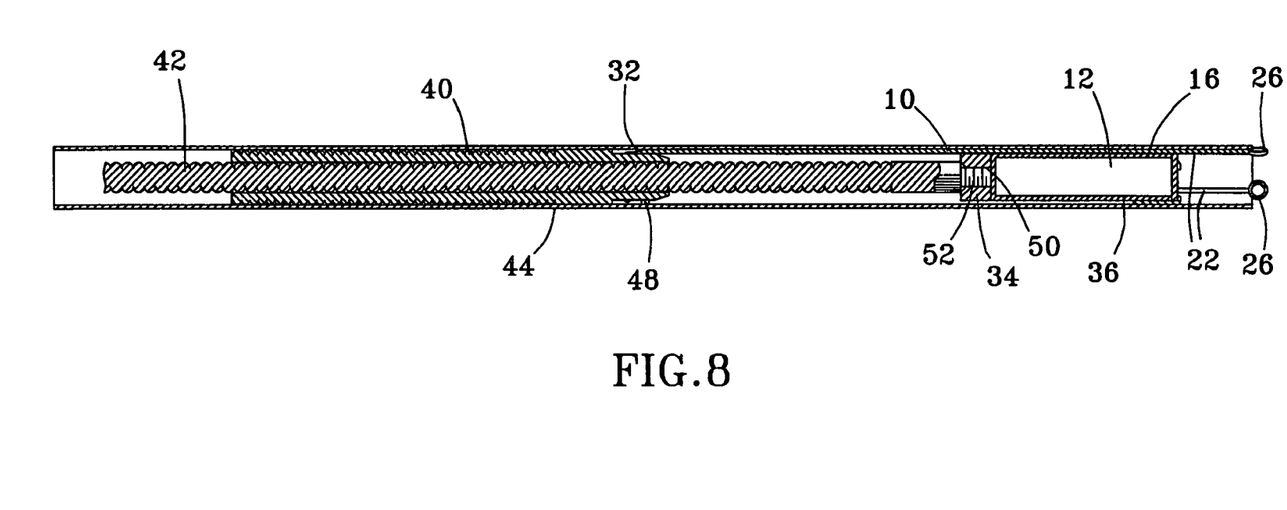

The first and second rings 32 and 34 are adapted to enable guidewires 40 and 42 to be coupled to the anchor 10, as seen in FIGS. 5, 7, and 8. Coupling of the guidewires 40 and 42 to the rings 32 and 34 can be accomplished in different ways including without limitation one, more, or any combination of the following methods: cam slot, threading, snapping, snap latch, latch fingers, spring latch, latch fingers with a catheter sheet on top to release the latch, use of one or more guidewires or catheters in order to either latch or release coupling means (such as latching fingers), dissolvable glues, temporary glues, thermal glues, heated shape memory latches, unheated shape memory latches, heated mechanical means, piezoelectric release system, hydraulic coupling systems, pneumatic coupling systems, magnetic coupling systems, etc. In the FIGS., the ring 32 is shown as being equipped with a cam slot 46 through which a peg 48 on the guidewire 40 passes before becoming latched with further rotation of the guidewire 40, while the second ring 34 is depicted as having internal threads 50 that threadably mate with external threads 52 on the end of the guidewire 42, as is a standard current practice in the cardiovascular field. The ring 34 and its internal threads 50 are coaxially aligned with the axis of the central body 16, as is the ring 32. The guidewire 40 has a tubular shape through which the guidewire 42 is able to reciprocate. The entire guidewire assembly is shown in FIGS. 5, 7, and 8 as being disposed in a delivery catheter 44 of a type known in the art. The configuration of the anchor 10 allows the anchor 10 and its implant 12 to be inserted inside the delivery catheter 44 and then positioned for insertion into the wall 14, and permits multiple tries to secure the anchor 10 in the desired location before deploying the arms 22 and arcuate members 24 and final detachment of the guidewires 40 and 42.

Figure 6:
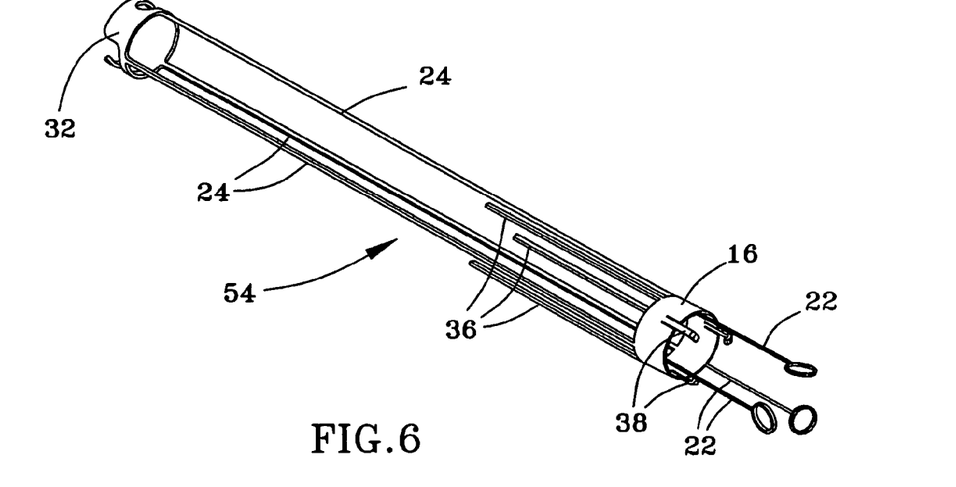
FIG. 6 is a perspective view of a preform from which the anchor of FIGS. 1 through 3 can be fabricated.
Figure 15:
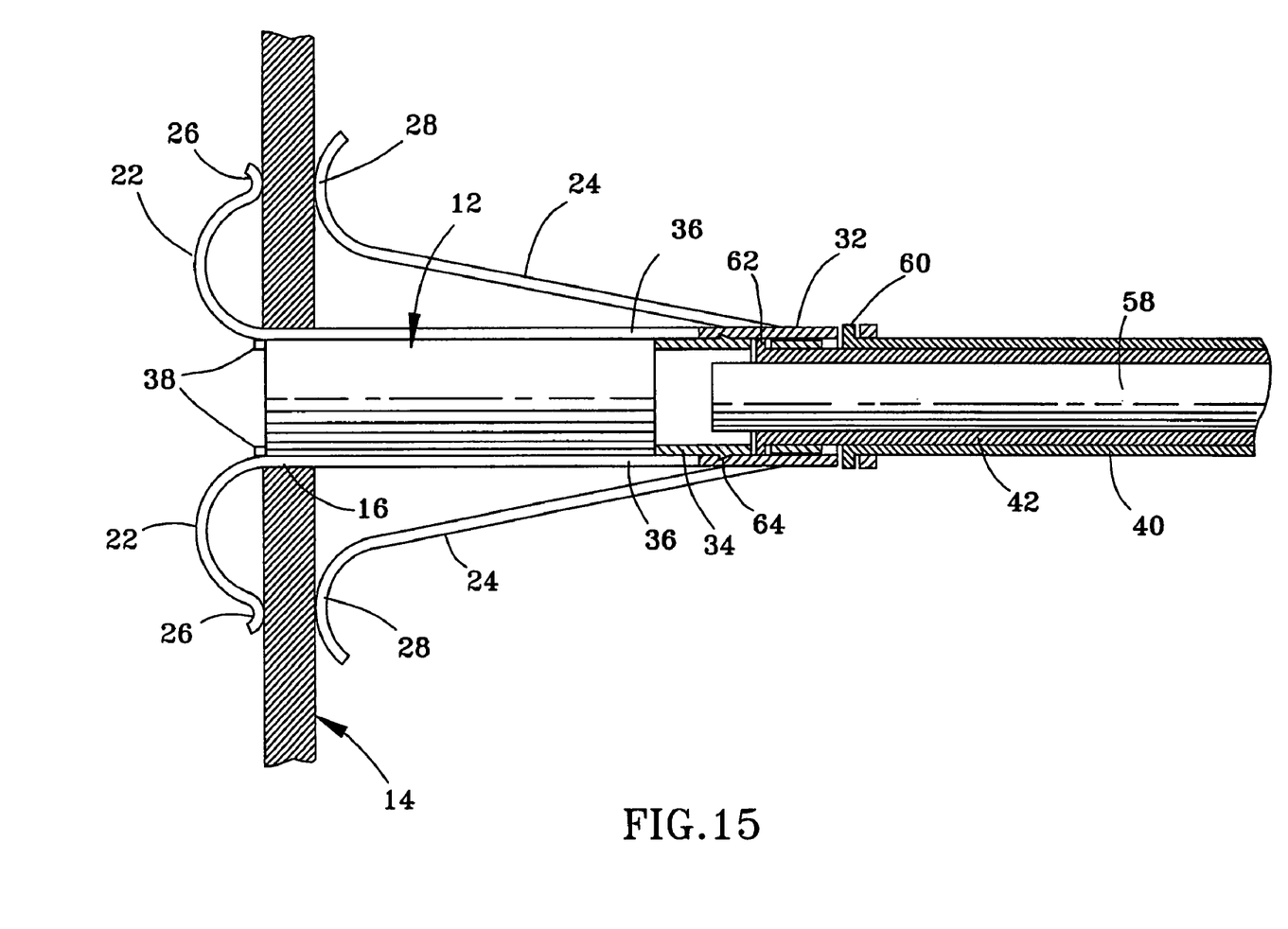
FIG. 15 is a cross-sectional view showing a medical implant anchored to a wall with an anchor in accordance with a second embodiment of this invention.

According to one aspect of the invention, one or more of the following components of the anchor 10 can be integral portions of a monolithic body: the central body 16, arms 22, arcuate members 24, first ring 32, second ring 34, and struts 36. For example, the central body 16, arms 22, arcuate members 24, first ring 32, and struts 36 can be formed from a monolithic body, while the second ring 34 is formed separately such that completing the anchor 10 requires only attachment of the second ring 34 to the struts 36, for example, by welding or another metallurgical joining technique. A preform 54 for this purpose is depicted in FIG. 6. Another and potentially preferable approach is represented in FIG. 15, which shows the central body 16, arms 22, struts 36, and second ring 34 as integral parts of a first monolithic body, and the arcuate members 24 and first ring 32 as integral parts of a second monolithic body that is joined or coupled to the first monolithic body. As represented in FIG. 15, the first ring 32 is telescoped over the second ring 34, and the rings 32 and 34 are interconnected with spring latches 64, though joining by other means is also possible, such as by welding. As such, the spring latches 64 are used to directly interconnect the rings 32 and 34, instead of through the arcuate members 24, central body 16, and struts 36 as done in the embodiment of FIGS. 1 through 5. In effect, the assemblage of the central body 16, struts 36, and rings 32 and 34 are functional equivalents of the central body 16 of FIGS. 1 through 5, such that the arcuate members 22 extend substantially radially from an end (second end 20 in FIGS. 1-5) of the central body that is defined by the ring 32 in FIG. 15.

Many existing medical implantable devices for use in the heart utilize NITINOL®, a "shape memory" nickel-titanium alloy that enables an umbrella-like structure folded inside a catheter for delivery to later automatically expand once outside the catheter for implantation. In a preferred embodiment, the anchor 10 is formed of NITINOL or another suitable shape memory material. According to another preferred aspect, the anchor 10 can be manufactured primarily by laser cutting techniques performed on solid tubes of a shape memory material, rather than primarily using welding techniques as typically done in the prior art. Fabrication of the anchor 10 using laser cutting techniques provides at least two important advantages. First, the reliability of the anchor 10 is much higher since its components (body 16, arms 22, arcuate members 24, ring 32, struts 36, and/or fingers 38) are integral portions of one or a limited number of monolithic metal pieces. Welded joints possess higher risk of failure than that possible with the preferred constructions for the anchor 10. Secondly, the cost of manufacturing can be significantly lower than would be possible if relying primarily on welding to form the anchor 10.

In practice, a NITINOL tube can be cut by laser alone to form the preform 54 depicted in FIG. 6, or to form two preforms for the two subcomponents for the embodiment depicted in FIG. 15. The laser cutting operation can be performed as an automated process based on drawing files using commercial mechanical design software. The tubular-shaped preform or preforms are then formed into a 3-D structure with shape memory by being placed in a mechanical jig and heated to an appropriate temperature to store the shape into the memory of the NITINOL material. In the case of the preform 54 of FIG. 6, the second ring 34 is then welded to the ends of the struts 36 to yield the structure shown in FIGS. 1 through 5. These welds are the only welds required by the anchor design of FIGS. 1 through 5. In the case of the embodiment of FIG. 15, welding can be completely eliminated as a process step.

A key parameter of any wireless, implantable system is the communication distance (both tele-powering and tele-communication) between the implant and the readout handheld unit. Since the anchor 10 may be formed of a metal such as NITINOL, there exists a potential that such a metallic anchor could adversely affect (reduce) the communication distance between the implant 12 and the handheld unit (not shown) by acting similar to a Faraday cage. Tests performed using metal implants indicated that telemetry communication distances can be reduced by about two-thirds, such that placing an implant using RF/electromagnetic telemetry inside a metal anchor would not be expected to achieve reasonable performance.

To overcome this problem, the anchor 10 is configured to avoid the primary causes of reduced communication distances. Attenuation was determined to depend on parameters including the number of metal loops, the orientation of the loops, and whether the loops are arranged in such a manner as to form a mesh or cage. Fewer numbers of metal loops were associated with longer communication distances. Furthermore, metal loops that are arranged in parallel to the implant communication coil (with or without a ferrite core) were found to not adversely affect the communication distance, while metal wires oriented perpendicular to the implant communication coil (with or without a ferrite core) were found to greatly reduce such magnetic fields. The anchor 10 of the present invention comprises few loops which are properly oriented and do not form a mesh. As seen in the Figures, the anchor 10 is able to make satisfactory use of only three sets of arms 22 and arcuate members 24. Furthermore, as discussed above, the arms 22 and arcuate members 24 of the anchor 10 are oriented to entirely lie within three planes whose intersection coincides with the axis of the anchor 10 and its implant 12. In this manner, the anchor 10 of this invention renders practical the use of small implants across long communication distances using a metallic anchor.

The anchor 10 may be employed to locate the implant 12 in various places, depending on the physiological parameter of interest. For the tailored treatment of chronic heart failure, LVEDP and/or MLA pressure are of most importance, and therefore the left chambers of the heart or immediately attaching vessels are among preferred locations for the implant 12. Because the number of implants is not practically limited by the technology, multiple locations for blood pressure measurement are easily established, including all chambers of the heart, major arteries and appendages. The preferred waveforms to monitor for CHF applications are the pressures of the left atrium. The monitored waveforms may include but not limited to complete detailed LA waveform, particularly accurate MLA pressure, real time, and continuous. It should be mentioned that some aspects of the anchor 10 described above will allow pressure measurements of the right atrium (by locating the pressure sensor at the end of the implant 12 facing the right atrium) or both right and left atriums (for example, using two pressure sensors, one at each end of the implant 12), or direct differential pressure measurement between the right and left atrium (again, for example, using two pressure sensors, one at each end of the implant 12). In addition to or instead of pressure, other parameters can easily be monitored using an implant delivered and placed with the anchor 10. Such parameters include but are not limited to blood chemistry, oxygen level, etc. For example, a hydrogel film (with selectivity to different elements) can be placed on top of a pressure sensor to measure the presence of elements that cause the hydrogel to expand, thereby applying pressure to the pressure sensor.

Thrombogenicity is the primary concern when considering a device for implantation in the left side of the heart, due to the possibility of thrombi reaching the brain. In order to assure such high-level of nonthrombogenicity, the present invention is able to reduce such risks through proper anchor shape, anchor location, and delivery method.

Thrombogenesis can be caused by direct chemical interaction with an implant or anchor, and by blood flow turbulence resulting from implant geometry. Regarding the former, the materials for the implant 12 and anchor 10 must be selected to be either biocompatible or the implant 12 and anchor 10 must be covered by biocompatible materials. As to the latter, the present invention provides an anchor configuration and placement capability that greatly reduces protrusion of the implant 12 and anchor 10 into the blood flow path of the left atrium to a minimum level, and also provides a hydrodynamic sensor profile that is minimally disruptive to surrounding blood flow. The implant 12 can be preferably placed with the anchor 10 of this invention at two desirable locations: the atrial septum and left atrial appendage. The atrial septum is believed to be preferable for locating the anchored implant 12. It should be emphasized that, while the implant may be long length (e.g., lengths greater than 10 mm), the anchor 10 is configured so that only a small portion (e.g., less than 2 mm) of the implant 12 is exposed to the left side of the heart; the rest of the implant 12 is in the septum wall and the right atrium. The pressure sensor is placed at or near the end side of the implant 12 that is exposed to the left side. A preferred location for the pressure sensor is believed to be on the front flat side of the cylindrical implant 12 shown in the Figures, so that only a small portion of the implant 12 will be above the surface of the left side of the heart. Subsequent cell growth over the top of the small exposed area of the implant 12 will further reduce the risk of thrombogenicity.

If placed in the atrial appendage, the implant 12 may be anchored by expanding the anchor 10 and then occluding the appendage. In this case, thrombi formation on the distal end (opposite from sensor) of the occlusion device would not pose a risk to the patient, as evidenced by previous left atrial appendage devices that have been introduced for this very purpose.

A reason for preferring placement in the atrial septum is that there exists FDA-approved, commercially-available medical devices for chronic implantation in this location. These devices, for example, are used to occlude atrial septum defects and other vascular holes. The implant 12 can be anchored to the atrial septum with similar techniques as FDA-approved, commercially-available devices such as the AMPLATZER® family of devices commercially available from AGA Medical, or the CardioSEAL commercially available from NMT Medical. These devices have been shown to be suitable for cardiovascular implantation. As a result, one may take advantage of this existing infrastructure, including standard practices of delivering cardiovascular implants. Another advantage of placing the implant 12 within the wall of the atrial septum is that the potential adverse confounding effects of the muscle contraction on the sampled pressure measurements will be considerably reduced.

Delivery of the implant 12 with the anchor 10 demands such considerations as safety, minimal invasiveness, suitability as an outpatient procedure, ease of operation, preferable use of existing practices, minimum training for the physician/technician, and the ability to allow multiple tries before deploying and releasing the anchor 10. The preferred delivery method for the anchor 10 is believed to be by catheter delivery, such as with the delivery catheter 44 depicted in FIG. 5. To minimize catheter diameter, the implant 12 is preferably small and thin. Delivery and placement of the anchor 10 is able to make use of standard current practices in the cardiovascular field to reduce both time and cost of R&D and manufacturing, create comfort and confidence in cardiologists, and make FDA process easier. The anchor 10 is configured so that, after it is inserted into the catheter 44, the diameter of the folded anchor 10 is equal or as close as possible to the diameter of the original tube from which the preform 54 was laser cut. This approach renders the smallest possible diameter of the delivery catheter 44.

Figures 9, 10, 11:
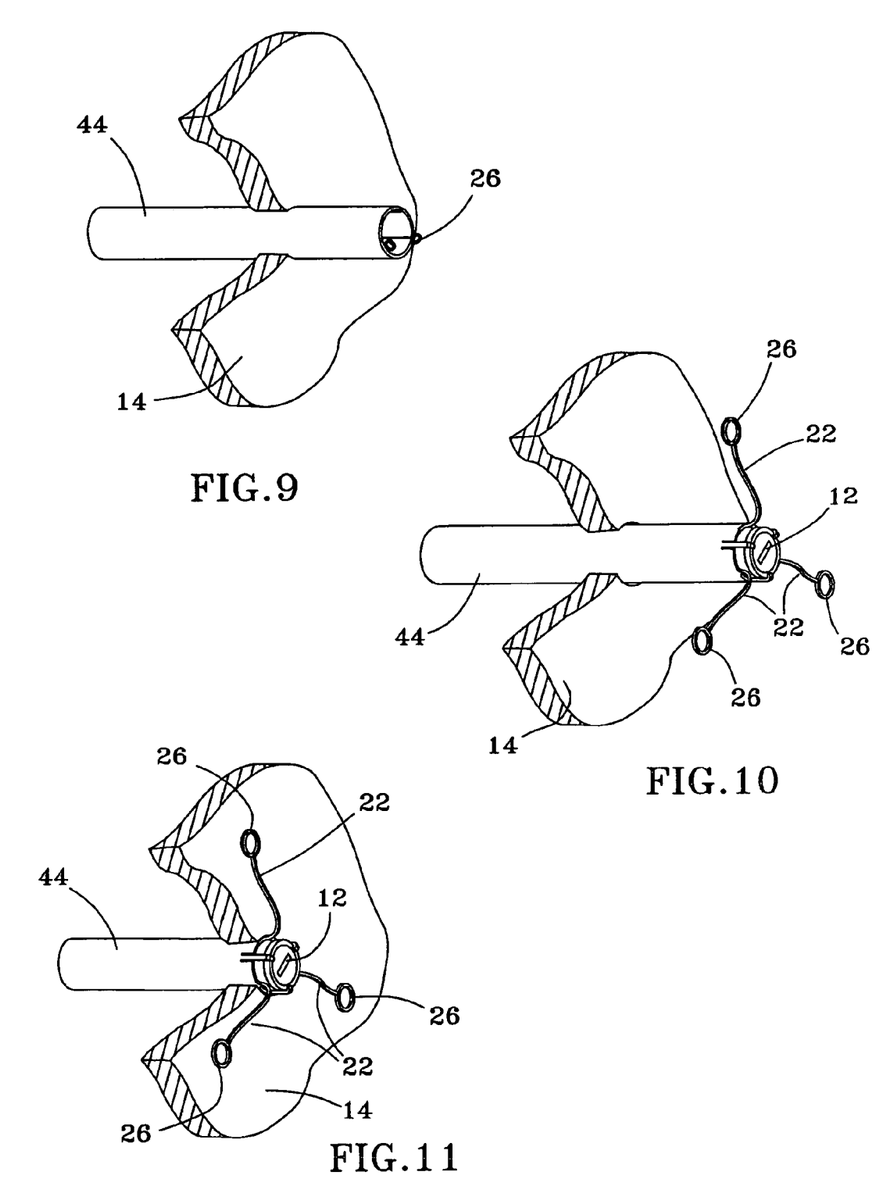
FIGS. 9 through 14 are perspective views representing procedural steps when placing the anchor and medical implant.
Figure 12:
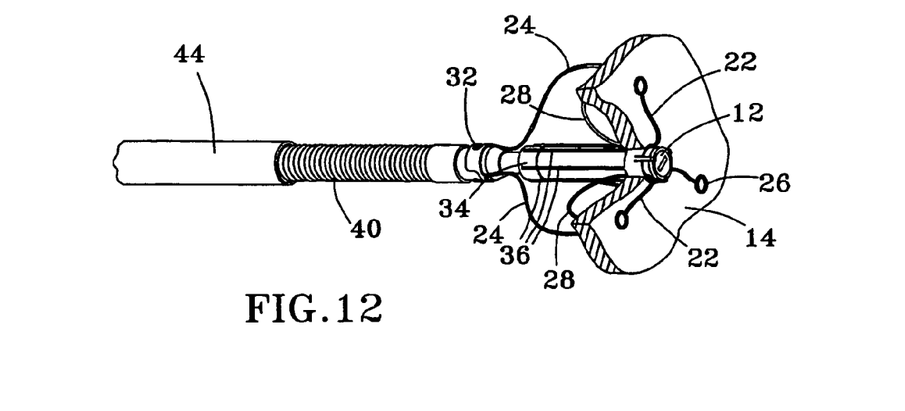
Figure 13:
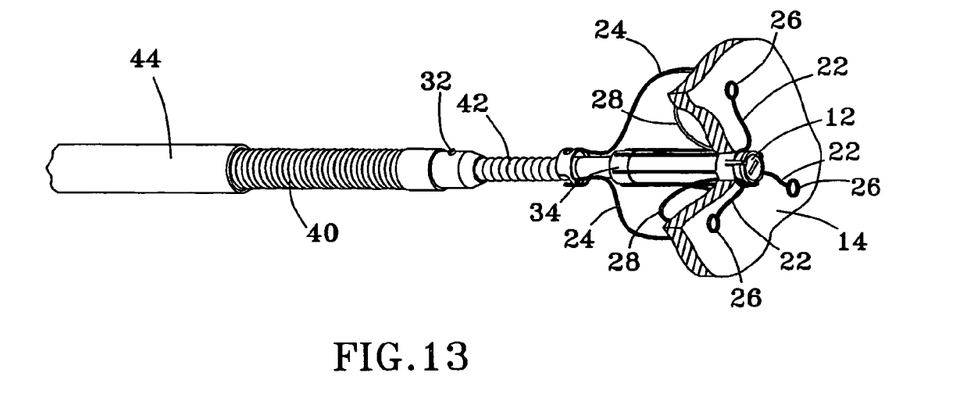
Figure 14:
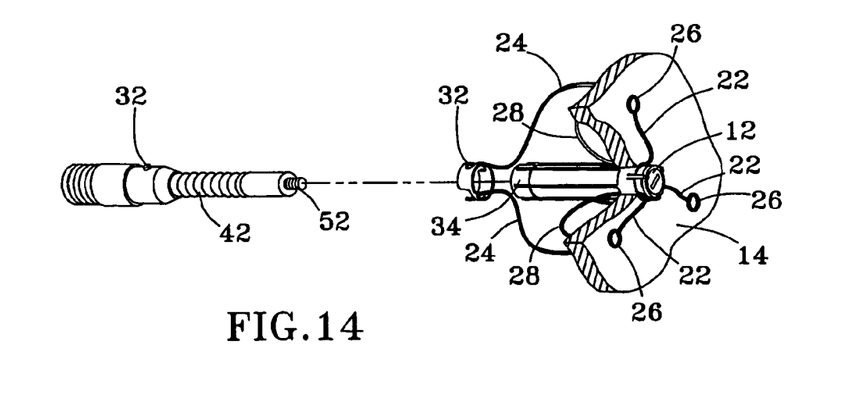

In the preferred configuration shown in FIG. 5, the delivery catheter 44 has the two guidewires 40 and 42 discussed above. The inner guidewire 42 is coupled to the second ring 34, while the outer tubular guidewire 40 is coupled to the first ring 32 of the anchor 10, as seen in FIG. 5. FIGS. 9 through 13 represent a series of steps depicting the procedure for delivering and implanting the anchor 10 and implant in the atrial septum 14. Using a standard cardiology guidewire via a standard procedure (not shown), the delivery catheter 44 is placed through the atrial septum 14. The anchor 10 is then inserted into the catheter 44. By slightly pulling the outer guidewire 40 away from the inner guidewire 42, the anchor 10 is straightened and roughly reacquires the original shape of its preform 54. FIG. 9 portrays this point of the delivery process, in which the pads 26 of the arms 22 protrude from the catheter 44. The anchor 10 is then pushed through the catheter 44 by grasping and pushing both guidewires 40 and 42 at the same time. The anchor 10 is pushed until the arms 22 are completely free of the catheter 44, such that the shape-memory property of the anchor material causes the arms 22 to expand with the pads 26 projecting back toward the atrial septum 14 as seen FIG. 10. Both guidewires 40 and 42 are then pulled back until the pads 26 rest on the left side of the atrial septum (FIG. 11). The catheter 44 is then retracted, causing the arcuate members 24 to be released on the side of the septum 14 opposite the arms 22. As with the arms 22, the shape-memory property of the anchor material causes the arcuate members 24 to expand so that their legs 28 project toward the atrial septum 14 as seen FIG. 12. The outer guidewire 40 can then be released by holding the inner guidewire 42 steady while the outer guidewire 40 is decoupled (FIG. 13). Finally, the inner guidewire 42 can be decoupled from the second ring 34, resulting in what is depicted in FIG. 14.

As an alternative to the above, the guidewires 40 and 42 may be latched to the rings 32 and 34 by means of flexible spring latching fingers 60 and 62 permanently attached to the guidewires 40 and 42, as depicted in the embodiment of FIG. 15. The latching fingers 60 and 62 are shown as being adapted to mate with corresponding recesses within the rings 32 and 34, respectively. FIG. 15 shows the latching fingers 60 and 62 as being held in the latched position by a central core element 58 held axially within the center of the guidewires 40 and 42. The core element 58 prevents the latching fingers 60 and 62 from disengaging the rings 32 and 34 during insertion of the anchor 10 and implant 12. The core element 58 can also be used to temporarily couple the rings 32 and 34 together during implantation, allowing the guidewires 40 and 42 to individually support the rings 32 and 34 while displaced axially apart from each other. The rings 32 and 34 are not locked together with the spring latches 64 until the arms 22 have been deployed. When this has been accomplished, the guidewire 40 can be used to push the ring 32 forward to radially spread the arcuate members 24 (which are cantilevered, in contrast to the embodiment of FIGS. 1-5), telescope the ring 32 over the ring 34, and finally latch the rings 32 and 34 together. With this approach, the guidewires 40 and 42 are decoupled from the rings 32 and 34, respectively, by retraction of the central core element 58 within the guidewires 40 and 42. As the core element 58 is withdrawn, the latching fingers 60 and 62 collapse radially inward toward the central axis of the guidewire assembly and disengage from rings 32 and 34.

In view of the above, the operator has the option to retry placing the anchor 10 and implant 12 any number of times before releasing the anchor 10 with the outer guidewire 40. The preferred use of two guidewires 40 and 42 is believed to be uncomplicated and readily within the skills of the ordinary cardiologist. Nonetheless, those skilled in the art will appreciate that the anchor 10 and its implant 12 could be delivered and placed with a single guidewire set.

In addition to the delivery and anchoring of wireless implanted medical devices, the anchor 10 and delivery method of this invention can be utilized for non-wireless applications. For example, a pressure sensor (or any other type of sensor) located in the left atrium (or elsewhere) can be provided with a communication connection to other medical devices (such as, but not limited to, pacemakers) from the right atrium side of the anchor/implant. Potential communication connections include, but are not limited to, electrical wires, pacemaker leads, flexible cables, optical connectors, ultrasonic pads, and electrophysiology signals. Hermetic electrical connection pads (instead of or in addition to a pressure sensor) can be provided from inside the implant 12 to its exterior. Such pads can be used to provide electrical connections to other medical devices, e.g., pacemakers, or provide electrical connections to other sensors (e.g., blood chemical sensors), which are made independently of the anchor 10 and implant 12. Preferred locations for these pads are believed to be either of the flat ends of the cylindrical implant 12 shown in the Figures, for locating the pads in the left side, right side, or both sides of the heart.

While the invention has been described in terms of certain embodiments, it is apparent that other forms could be adopted by one skilled in the art. Therefore, the scope of the invention is to be limited only by the following claims.

The invention claimed is:

1. An anchor for a medical implant, the anchor comprising:
    a central body comprising an annular-shaped body and having an axis, a bore for receiving the medical implant, and first and second ends in oppositely-disposed first and second axial directions, respectively, along the axis of the central body, the bore having an opening at the first end of the central body for receiving the medical implant in the second axial direction;
    means for retaining the medical implant within the bore of the central body;
    a plurality of arms and a plurality of members extending from the central body;
    a first ring spaced axially from the annular-shaped body in the second axial direction, the members extending radially from the first ring;
    a second ring between the first ring and the annular-shaped body; and
    struts securing the second ring to the annular-shaped body, the medical implant being disposable within the annular-shaped body and the struts and securable therein by the retaining means;
    the anchor having a deployed configuration wherein:
        the arms extend substantially radially from the first end of the central body, each of the arms having a distal portion extending in the second axial direction relative to the central body; and
        the members extend radially from the central body, each of the members defining a leg extending in the first axial direction toward the distal portions of the arms.

2. An anchor according to claim 1, wherein the retaining means is disposed at the first end of the central body and partially closes the opening of the bore to secure the medical implant within the bore.

3. An anchor according to claim 1, wherein each of the arms and members lies in a plane parallel to the axis of the central body.

4. An anchor according to claim 1, wherein each of the arms is axially aligned with a corresponding one of the members, and the distal portions of the arms oppose the legs of the members.

5. An anchor according to claim 1, wherein the anchor has not more than three of the arms and not more than three of the members.

6. An anchor according to claim 1, wherein the distal portions of the arms are pads oriented substantially transverse to the axis of the central body.

7. An anchor according to claim 1, wherein the first ring is secured to the central body by the members.

8. An anchor according to claim 7, wherein the first ring comprises means for coupling a guidewire thereto.

9. An anchor according to claim 8, wherein the coupling means comprises at least one element selected from the group consisting of cam slots, threads, snaps, snap latches, latch fingers, spring latches, latch fingers with a catheter sheet for releasing the latch, guidewires, catheters, dissolvable glues, temporary glues, thermal glues, heated shape memory latches, unheated shape memory latches, heated mechanical means, piezoelectric release systems, hydraulic coupling systems, pneumatic coupling systems, and magnetic coupling systems.

10. An anchor according to claim 1, wherein the second ring is spaced axially from the second end of the central body.

11. An anchor according to claim 10, wherein the second ring comprises means for coupling a guidewire thereto.

12. An anchor according to claim 11, wherein the coupling means comprises at least one element selected from the group consisting of cam slots, threads, snaps, snap latches, latch fingers, spring latches, latch fingers with a catheter sheet for releasing the latch, guidewires, catheters, dissolvable glues, temporary glues, thermal glues, heated shape memory latches, unheated shape memory latches, heated mechanical means, piezoelectric release systems, hydraulic coupling systems, pneumatic coupling systems, and magnetic coupling systems.

13. An anchor according to claim 1, wherein each of the first and second rings comprises means for coupling a guidewire thereto.

14. An anchor according to claim 13, wherein the coupling means of the second ring comprises threads and the coupling means of the first ring comprises a cam slot.

15. An anchor according to claim 1, wherein the first ring comprises means for coupling a guidewire thereto.

16. An anchor according to claim 1, wherein the second ring comprises means for coupling a guidewire thereto.

17. An anchor according to claim 1, wherein the central body, the arms, and the members are integral portions of a monolithic body.

18. An anchor according to claim 17, wherein laser cutting of a tube is used to produce the integral portions of the monolithic body.

19. An anchor according to claim 1, wherein the central body, the arms, the members, and the first ring are integral portions of a monolithic body.

20. An anchor according to claim 1, wherein the central body, the arms, the members, and the struts are integral portions of a monolithic body, and the second ring is metallurgically joined to the struts.

21. An anchor according to claim 20, wherein laser cutting of a tube is used to produce the integral portions of the monolithic body.

22. An anchor according to claim 1, wherein one or more of the following are integral portions of a monolithic body: the central body, the arms, the members, the struts, and the first ring.

23. An anchor according to claim 1, wherein the annular-shaped body, the arms, and the second ring are integral portions of a first monolithic body, and the members and the first ring are integral portions of a second monolithic body which is joined or coupled to the first monolithic body.

24. An anchor according to claim 23, wherein laser cutting of at least one tube is used to produce the integral portions of the first and second monolithic body.

25. An anchor according to claim 1, wherein at least the arms and the members are formed of a shape-memory material.

26. A method of manufacturing the anchor according to claim 1, the method comprising the step of machining a monolithic body to form the central body, the arms, and the members.

27. A method of manufacturing the anchor according to claim 1, the method comprising the steps of:
    machining a first monolithic tubular body to form the central body and the arms;
    machining a second monolithic tubular body to form the members; and
    attaching the second monolithic body to the first monolithic body.

28. A method according to claim 27, wherein the machining step is a laser cutting operation.

29. An anchor according to claim 1, wherein the implant is received within and secured to the central body, and the implant is communicatively connected to a medical device.

30. An anchor according to claim 29, wherein the medical device is a pacemaker.

31. An anchor according to claim 29, wherein the implant is communicatively connected to the medical device by a communication connection selected from the group consisting of electrical wires, pacemaker leads, flexible cables, optical connectors, ultrasonic pads, and electrophysiology signals.

32. An anchor for a cardiovascular implant, the anchor comprising:
    a central body in which the cardiovascular implant is received, the central body having an axis and first and second ends in oppositely-disposed first and second axial directions, respectively, along the axis of the central body;
    a plurality of arcuate arms extending from the first end of the central body;
    a first ring spaced axially from the second end of the central body;
    a plurality of arcuate members extending from the first ring toward the central body;
    a second ring spaced axially from the second end of the central body and located between the central body and the first ring; and
    means for securing the second ring to the central body;
    wherein the cardiovascular implant is disposed within the central body and the securing means so that an axial end thereof axially abuts the second ring, and the anchor has a deployed configuration wherein the arcuate arms extend substantially radially from the first end of the central body, each of the arcuate arms has a distal portion extending in the second axial direction relative to the central body, the arcuate members extend radially from the second end of the central body, and each of the arcuate members defines a leg extending in the first axial direction toward the distal portions of tile arcuate arms.

33. An anchor according to claim 32, wherein the anchor further comprises means disposed at the first end of the central body for abutting an axial end of the cardiovascular implant opposite the axial end of the cardiovascular implant abutting the second ring.

34. An anchor according to claim 32, wherein each of the arcuate arms and arcuate members lies in a plane containing the axis of the central body.

35. An anchor according to claim 34, wherein each of the arcuate arms is axially aligned with a corresponding one of the arcuate members, and the distal portions of the arcuate arms oppose the legs of the arcuate members.

36. An anchor according to claim 32, wherein the anchor has not more than three of the arcuate arms and not more than three of the arcuate members.

37. An anchor according to claim 32, wherein the distal portions of the arcuate arms are oriented substantially transverse to the axis of the central body.

38. An anchor according to claim 32, wherein the first ring comprises means for coupling a guidewire thereto.

39. An anchor according to claim 32, wherein the second ring comprises means for coupling a guidewire thereto.

40. An anchor according to claim 32, wherein two or more of the following are integral portions of a monolithic body: the central body, the arcuate arms, the arcuate members, the first ring, the second ring, and the securing means.

41. An anchor according to claim 32, wherein the central body, the arcuate arms, the second ring, and the securing means are integral portions of a monolithic body.

42. An anchor according to claim 41, wherein the securing means comprise a plurality of struts extending from the second end of the central body.

43. An anchor according to claim 41, wherein laser cutting of a tube is used to produce the integral portions of the monolithic body.

44. An anchor according to claim 32, wherein the central body, the arcuate arms, the second ring, and the securing means are integral portions of a first monolithic body, and the arcuate members and the first ring are integral portions of a second monolithic body which is joined or coupled to the first monolithic body.

45. An anchor according to claim 44, wherein laser cutting of a tube is used to produce the integral portions of the first and second monolithic bodies.

46. An anchor according to claim 32, wherein at least the arcuate arms and the arcuate members are formed of a shape-memory material.

47. A method of manufacturing the anchor according to claim 32, the method comprising the step of machining a monolithic body to form the central body, the arms, the second ring, and the securing means.

48. A method according to claim 47, wherein the machining step is a laser cutting operation.

49. A method of manufacturing the anchor according to claim 32, the method comprising the step of machining a monolithic body to form the members and the first ring.

50. A method according to claim 49, wherein the machining step is a laser cutting operation.

51. A method of manufacturing the anchor according to claim 32, the method comprising the steps of:
   machining a first monolithic body to form the central body, the arms, the second ring, and the securing means;
   machining a second monolithic body to form the members and the first ring; and
   attaching the second monolithic body to the first monolithic body.

52. A method according to claim 51, wherein each of the machining steps is a laser cutting operation.

* * * * *